US008268359B2

(12) United States Patent
Pradeep et al.

(10) Patent No.: US 8,268,359 B2
(45) Date of Patent: Sep. 18, 2012

(54) ORGANIC POLYMER-INORGANIC FINE PARTICLE ANTIMICROBIAL COMPOSITES AND USES THEREOF

(75) Inventors: Thalappil Pradeep, Tamilnadu (IN); A. Sreekumaran Nair, Thiruvananthapuram (IN)

(73) Assignee: Indian Institute of Technology Madras, Tamilnadu (IN)

( * ) Notice: Subject to any disclaimer, the term of this patent is extended or adjusted under 35 U.S.C. 154(b) by 269 days.

(21) Appl. No.: 12/639,403

(22) Filed: Dec. 16, 2009

(65) Prior Publication Data

US 2011/0052714 A1    Mar. 3, 2011

(30) Foreign Application Priority Data

Aug. 26, 2009  (IN) ............................ 2052/CHE/2009

(51) Int. Cl.
*A61K 9/16*    (2006.01)
*A01N 59/16*   (2006.01)
*A01N 33/24*   (2006.01)
*A01N 55/02*   (2006.01)

(52) U.S. Cl. ......... 424/497; 424/617; 424/618; 514/495
(58) Field of Classification Search .................. 424/497, 424/617, 618; 514/495
See application file for complete search history.

(56) References Cited

U.S. PATENT DOCUMENTS

| 5,853,886 | A | 12/1998 | Pinnavaia et al. |
| 6,040,111 | A * | 3/2000 | Karasawa et al. ......... 430/270.1 |
| 6,224,898 | B1 | 5/2001 | Balogh et al. |
| 6,544,651 | B2 | 4/2003 | Wong et al. |
| 6,579,906 | B2 | 6/2003 | Cooper et al. |
| 6,593,408 | B1 | 7/2003 | Takaki et al. |
| 6,599,631 | B2 * | 7/2003 | Kambe et al. ................. 428/447 |
| 6,646,026 | B2 | 11/2003 | Fan et al. |
| 6,710,111 | B2 | 3/2004 | Kuo et al. |
| 6,818,081 | B2 | 11/2004 | Gash et al. |
| 7,112,369 | B2 | 9/2006 | Wang et al. |
| 7,115,688 | B1 | 10/2006 | Mirkin et al. |
| 7,226,966 | B2 | 6/2007 | Kambe et al. |
| 7,253,004 | B2 | 8/2007 | Vossmeyer et al. |
| 7,306,777 | B2 * | 12/2007 | Bringley et al. ............. 423/306 |
| 2005/0270442 | A1 * | 12/2005 | Yang et al. ...................... 349/86 |
| 2007/0166224 | A1 | 7/2007 | Sreekumaran et al. |
| 2009/0149583 | A1 | 6/2009 | Lin et al. |
| 2010/0175747 | A1 * | 7/2010 | Segato et al. .................. 136/256 |

FOREIGN PATENT DOCUMENTS

| IN | 200767 | 2/2007 |
| WO | 2005070534 A1 | 8/2005 |

OTHER PUBLICATIONS

Trabelsi et al., Synthetic Metals, 2005, 151, 19-24.*
Dridi et al., Materials Science and Engineering C, 2006, 26, 415-420.*
Bergaoui et al., European Polymer Journal, 2002, 38, 1731-1738.*
Xu, X. et al., "Fabrication of Biodegradable Electrospun Poly(L-lactide-co-glycolide) Fibers with Antimicrobial Nanosilver Particles," Journal of Nanoscience and Nanotechnology, 2008, vol. 8, pp. 5066-5070.
Chen, M. et al., "Preparation and Study of Polyacryamide-Stabilized Silver Nanoparticles through a One-Pot Process," Journal of Chemistry B, 2006, vol. 110, No. 23, pp. 11224-11231.
International Preliminary Report on Patentability for Intl. Pat. Appln. No. PCT/IB2010/002016, issued on Feb. 28, 2012, 8 pp.
International Search Report and Written Opinion for Intl. Pat. Appln. No. PCT/IB2010/002016, mailed on Nov. 30, 2010, 12 pp.
Nair, A.S. et al.,"Organic-Soluble Antimicrobial Silver Nanoparticle-Polymer Composites in Gram Scale by One-Pot Synthesis," Applied Materials and Interfaces, 2009, vol. 1, No. 11, pp. 2413-2419.
Sharma, V.K. et al., "Silver nanoparticles: Green synthesis and their antimicrobial activities," Advances in Colloid and Interface Science, 2009, vol. 145, pp. 83-96.
Zhang, Z. et al., "A convenient route to polyacrylonitrile/silver nanoparticle composite by simultaneous polymerization-reduction approach," Polymer, Sep. 2001, vol. 42, No. 19, pp. 8315-8318.
Zodrow Katherine, Brunet Lena, Mahendra Shaily, Li Dong, Zhang Anna, Li Qilin and Alvarez Pedro J., "Polysulfone Ultrafiltration Membranes Impregnated with Silver Nanoparticles Show Improved Biofouling Resistance and Virus Removal", Water Research, 2009, vol. 43, pp. 715-723.
Kumar Ashavani, Vemula Praveen Kumar, Mayan Pulickel M. and John George, "Silver-Nanoparticle-Embedded Antimicrobial Paints Based on Vegetable Oil", Nature Materials, Jan. 20, 2008, vol. 7, pp. 1-6.
Balogh Lajos, Swanson Douglas R., Tomalia Donald A., Hagnauer Gary L. and McManus Albert T., "Dendrimer-Silver Complexes and Nanocomposites as Antimicrobial Agents", Nano Letters, 2001, vol. 1, No. 1, pp. 18-21. doi: 10.1021/nl005502p.
Pintér Enikő, Patakfalvi Rita, Fülei Tamás, Gingl Zoltán, Dékany Imre and Visy Csaba, "Characterization of Polypyrrole-Silver Nanocomposites Prepared in the Presence of Different Dopants", Journal of Physical Chemistry B, Sep. 22, 2005, vol. 109, No. 37, pp. 17474-17478.
Hasell Tom, Thurecht Kristofer J., Jones Rhys D. W., Brown Paul D. and Howdle Steven M., "Novel One Pot Synthesis of Silver Nanoparticle-Polymer Composites by Supercritical Co2 Polymerisation in the Presence of a RAFT Agent", Chemical Communications, Oct. 14, 2007, pp. 3933-3935.
Oliveira Marcela M., Castro Eryza G., Canestraro Carla D., Zanchet Daniela, Ugarte Daniel, Roman Lucimara S., and Zarbin Aldo J. G., "A Simple Two-Phase Route to Silver Nanoparticles/Polyaniline Structures", Journal of Physical Chemistry B, Aug. 31, 2006, vol. 110, No. 34, pp. 17063-17069.
Mbhele Z. H., Salemane M.G., Sittert C. G. C. E. Van, Nedeljkovic J.M., Djokovic V. and Luyt A.S., "Fabrication and Characterization of Silver-Polyvinyl Alcohol Nanocomposites", Chemistry of Materials, 2003, vol. 15, No. 26, pp. 5019-5024.
Jain Prashant and Pradeep T., "Potential of Silver Nanoparticle-Coated Polyurethane Foam as an Antibacterial Water Filter", Biotechnology and Bioengineering, 2005, vol. 90, pp. 59-63.

(Continued)

*Primary Examiner* — Abigail Fisher
(74) *Attorney, Agent, or Firm* — Foley & Lardner LLP

(57) ABSTRACT

An embodiment relates to a composition comprising a noble-metal containing nanoparticle and a polymer located on a surface of the nanoparticle, wherein the polymer is a polycondensation product of a halogenated monomer. Other embodiments relate to the method of making a composition and providing antimicrobial treatment using the composition.

17 Claims, 7 Drawing Sheets

OTHER PUBLICATIONS

Manna Swarup, Batabyal Sudip K. and Nandi Arun K., "Preparation and Characterization of Silver-Poly (vinylidene fluoride) Nanocomposites: Formation of Piezoelectric Polymorph of Poly(vinylidene fluoride)", Journal of Physical Chemistry B, 2006, vol. 110, No. 25, pp. 12318-12326.

Karim Mohammad Rezaul, Lim Kwon Taek, Lee Chul Jae, Bhuiyan MD Tauhidul Islam, Kim Hee Jin, Park Lee-Soon and Lee Mu Sang, "Synthesis of Core-Shell Silver-Polyaniline Nanocomposites by Gamma Radiolysis Method", Journal of Polymer Science Part A: Polymer Chemistry, Dec. 15, 2007, vol. 45, Issue 24, pp. 5741-5747.

Liu Huarong, Ge Xuewu., Ni Yonghong., Ye Qiang and Zhang Zhicheng., Synthesis and Characterization of Polyacrylonitrile-Silver Nanocomposites by Gamma-Irradiation, Radiation Physics and Chemistry, Apr. 2001, vol. 61, pp. 89-91.

Nair A. Sreekumaran, Tom Renjis T. and Pradeep T., "Detection and Extraction of Endosulfan by Metal Nanoparticles", Journal of Environmental Monitoring, 2003, vol. 5, pp. 363-365.

Nair A. Sreekumaran and Pradeep T., "Extraction of Chlorpyrifos and Malathion from Water by Metal Nanoparticles", Journal of Nanoscience and Nanotechnology, 2007, vol. 7, pp. 1-7.

Nair A. Sreekumaran and Pradeep T., "Halocarbon Mineralization and Catalytic Destruction by Metal Nanoparticles," Current Science, Jun. 25, 2003, vol. 84, No. 12, pp. 1560-1564.

Winey K.I. and Vaia R.A., "Polymer Nanocomposites", MRS Bulletin, 2007, vol. 32, pp. 314-322.

Freemantle Michael, "Fluoropolymer Breakthrough", Chemical and Engineering News, Sep. 4, 2000, CENEAR, vol. 78, No. 36, pp. 11-12.

* cited by examiner

Average zone of inhibition width ~ 2.5 mm

FIG. 4: A and B

FIG. 5: A and B

FIG. 7: A and B
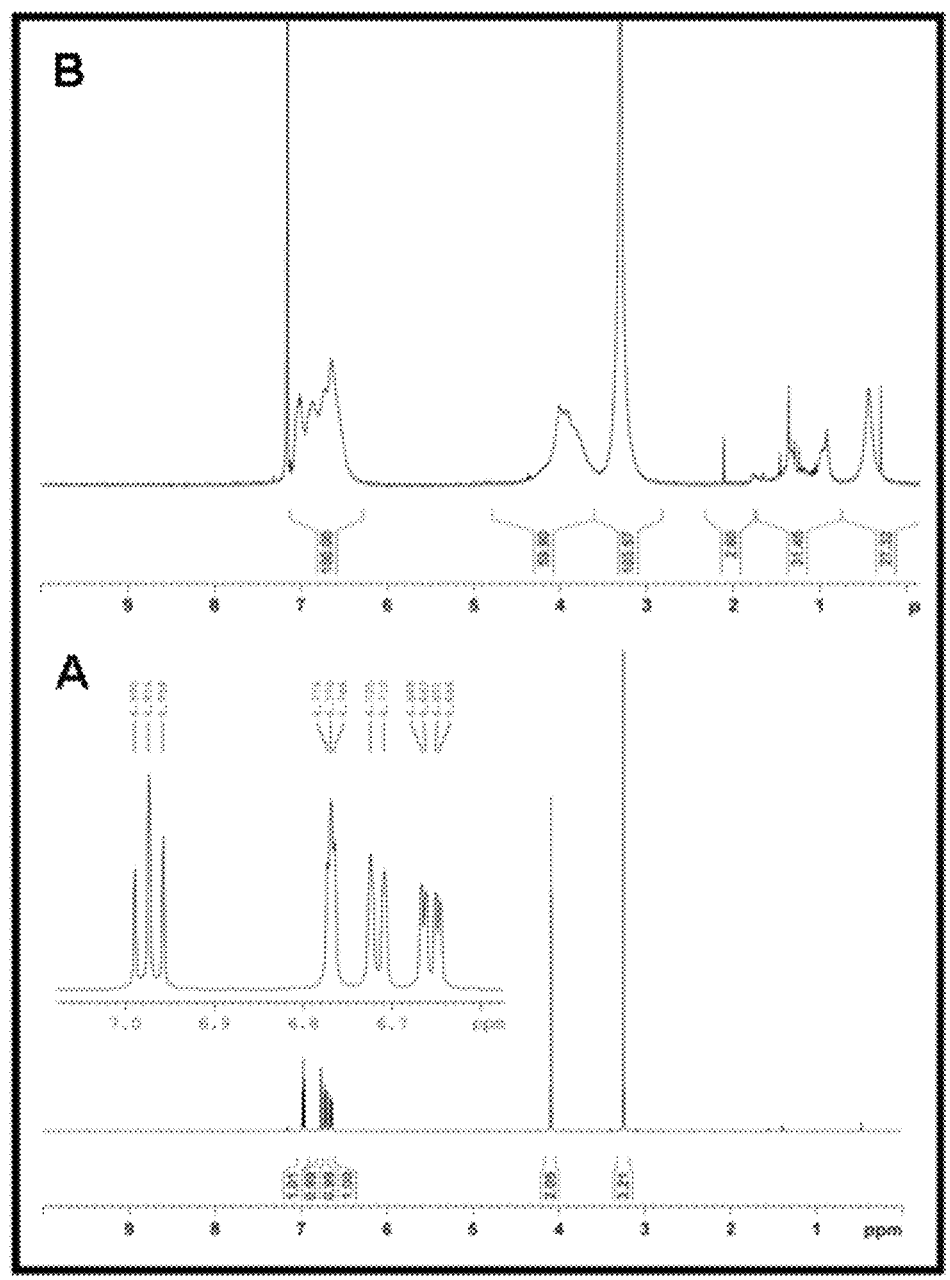

ORGANIC POLYMER-INORGANIC FINE PARTICLE ANTIMICROBIAL COMPOSITES AND USES THEREOF

CROSS-REFERENCE TO RELATED APPLICATIONS

The present application claims the benefit of Indian Patent Application No. 2052/CHE/2009, filed Aug. 26, 2009, which is hereby incorporated by reference in its entirety.

BACKGROUND

Silver (Ag) nanoparticles find applications in fields ranging from healthcare, defense and day-to-day life. For these applications, stability and complete dispersibility of the Ag nanoparticles in a solvent is essential and this is one of the most challenging problems limiting their widespread application. One way of protecting the nanoparticles and increasing their solubility is by polymer stabilization. Polymer stabilization enhances the stability and processibility of the nanoparticles to a great extent for industrial applications. However, there are only a few methods for the synthesis of organic soluble silver nanoparticle-polymer composites (Ag-PNCs), and all of the methods either involve multistep synthetic procedures or costly chemicals.

SUMMARY

The embodiments herein relate to a composition comprising a noble-metal containing nanoparticle and a polymer located on a surface of the nanoparticle, wherein the polymer is a polycondensation product of a halogenated monomer. Preferably, the composition exhibits an antimicrobial activity. Preferably, the composition dissolves in an organic solvent. Preferably, the composition is configured to be dried and dissolved multiple times without affecting physical and chemical characteristics of the nanoparticle. Preferably, the nanoparticle comprises silver and the monomer comprises an alkoxybenzyl halide. Preferably, the polymer comprises poly (alkoxybenzyl). Preferably, the polymer is located directly on the surface of the nanoparticle, wherein the nanoparticle comprises silver.

Another embodiment relates to a method comprising creating polycondensation of a halogenated monomer and forming a polymer on a surface of a noble-metal containing nanoparticle, wherein the method is carried out in a single vessel. Preferably, the method is carried out at about room temperature. Preferably, the polycondensation comprises a chemical condensation reaction leading to a formation of the polymer by polymerizing the monomer and releasing water or a molecule. Preferably, the nanoparticle comprises silver and the monomer comprises alkoxybenzyl halide. Preferably, the forming the polymer is carried out without a presence of an external catalyst during the polycondensation of the monomer. Preferably, the polymer is located directly on the surface of the nanoparticle, wherein the nanoparticle comprises silver.

Another embodiment relates to a method comprising treating a material with a composition comprising a noble-metal containing nanoparticle and polymer is located on a surface of the nanoparticle, wherein the polymer is a polycondensation product of a halogenated monomer. Preferably, the treating is an antimicrobial treatment. Preferably, the material is selected from water, waste water, a military equipment, a civilian protection equipment, a soft drink, a detergent, a medical product, an electrical component, an electronics component, and combinations thereof. Preferably, the treating comprises applying a film or a coating on the material, the film or the coating comprising the composition. Preferably, the treating comprises reducing an amount of bacteria and/or fungi in or on the material. Preferably, the antimicrobial treatment produces antimicrobial activity that persists for at least one month. Preferably, the nanoparticle comprises silver and the monomer comprises alkoxybenzyl halide.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE FIGURES

FIG. 7A shows the NMR spectrum of 2-methoxybenzyl chloride and FIG. 7B shows the NMR spectrum of the Ag-PNC formed from the 2-methoxybenzyl chloride monomer.

DETAILED DESCRIPTION

Figure 1:
FIG. 1 is a photograph of a silver nanoparticle-polymer composite (Ag-PNC) in toluene.

The embodiments relate to a noble-metal containing nanoparticle-polymer composite.

Noble metal refers to the metals of groups 9, 10 and 11 of transition metal series in the periodic table (of the IUPAC style). The noble metal of the noble-metal containing nanoparticle includes rhodium, iridium, palladium, silver, osmium, iridium, palladium, platinum, gold or combinations thereof.

Nanoparticle refers to a particle having at least one dimension sized between 1 and 100 nanometers.

A monomer is a small molecule that may become chemically bonded to other monomers to form a polymer. Typically, in the context of the present invention, a monomer is an organic monomer containing carbon and halogen.

A polymer is a large molecule composed of repeating structural units typically connected by covalent chemical bonds. The repeating structural units are monomer residues of one or more monomers that have undergone polymerization reaction to form the polymer.

Polycondensation or condensation polymerization refers to polymerizations in which bi-functional or multifunctional monomers react to form dimers, trimers, longer oligomers and eventually long chain polymers.

An antimicrobial is a substance that kills or inhibits the growth of microorganisms such as bacteria, fungi, or protozoa, as well as destroying viruses.

The "antimicrobial activity" refers to the antimicrobial action of an antimicrobial substance.

The term "static antimicrobial activity" means that the antimicrobial action persists for several months.

A halogenated monomer is a monomer that contains at least one halogen, which is a member of the series of non-metal elements from Group 17 IUPAC Style (formerly: VII, VIIA) of the periodic table, comprising fluorine, (F); chlorine, (Cl); bromine, (Br); iodine, (I); and astatine, (At).

An embodiment relates to silver nanoparticle-polymer composites (Ag-PNCs) having excellent antimicrobial activity. In one embodiment, the structure of Ag-PNCs is:

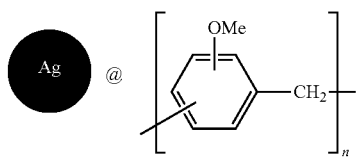

In the description above, '@' implies that the polymer on the right side of @ is covering the nanoparticle labeled, 'Ag'.

The embodiments herein provide a simple, low-cost and environmentally benign one-pot method to synthesize organic soluble Ag-PNCs at room temperature wherein the polymer is formed on the surfaces of nanoparticles due to the nanoparticles'-catalyzed polycondenzation. The term "one-pot" means a single reaction vessel. For example, in an embodiment, a desired amount of the synthesized Ag nanoparticles (Ag-citrate) is mixed with an alcohol in a round bottomed (RB) flask. A desired amount of the alkoxybenzyl halide is then added to the mixture and kept for stirring. Polycondensation of the alkoxybenzyl halide occurs on the surfaces of the silver nanoparticles, which precipitates from the reaction medium. The resulting brownish precipitate is an Ag-PNC, which could be freely dissolved in organic solvents.

The monomers polymerize on the nanoparticles' surfaces by polycondensation. Monomers that could be used for the polycondensation polymer include alkoxybenzyl halides (2-methoxybenzyl chloride, 3-methoxybenzyl chloride, 4-methoxybenzyl chloride, and their bromides and iodides and ethoxy derivatives), alkylbenzyl halides (4-methylbenzyl chloride, 2-methylbenzyl chloride, 2,4-dimethylbenzyl chloride, 2,4,6-trimethylbenzyl chloride, and other alkyl derivatives), hydroxybenzyl halides (2, 3 and 4-hydroxybenzyl halides), and halohydroxybenzyl halides.

The Ag-PNCs can be freely dissolved in common organic solvents at room temperature so that they can be incorporated in any common polymer or plastic or paint. The Ag-PNC solutions can be easily made into thin films (by dip coating), freestanding films or painted on substrates. The Ag-PNCs can be painted on substrates to get thin films and coatings. The Ag-PNCs are stable for years without any physical or chemical changes to the nanoparticles. The Ag-PNCs can be dried and re-dissolved several times without affecting the physical and chemical characteristics of the nanoparticles. A photograph of the Ag-PNC in toluene ($C_6H_5$-$CH_3$) is shown in FIG. 1. Ag-PNCs of the embodiments herein are also soluble in solvents such as alkyl halides, aryl halides, aromatic hydrocarbons, tetrahydrofuran (THF), dimethyl formamide (DMF), benzene ($C_6H_6$), dimethyl sulfoxide (DMSO having the formula ($CH_3$)$_2$SO), chlorobenzene ($C_6H_5$Cl), dichloromethane ($CH_2Cl_2$) and trichloromethane ($CHCl_3$).

Figure 2:
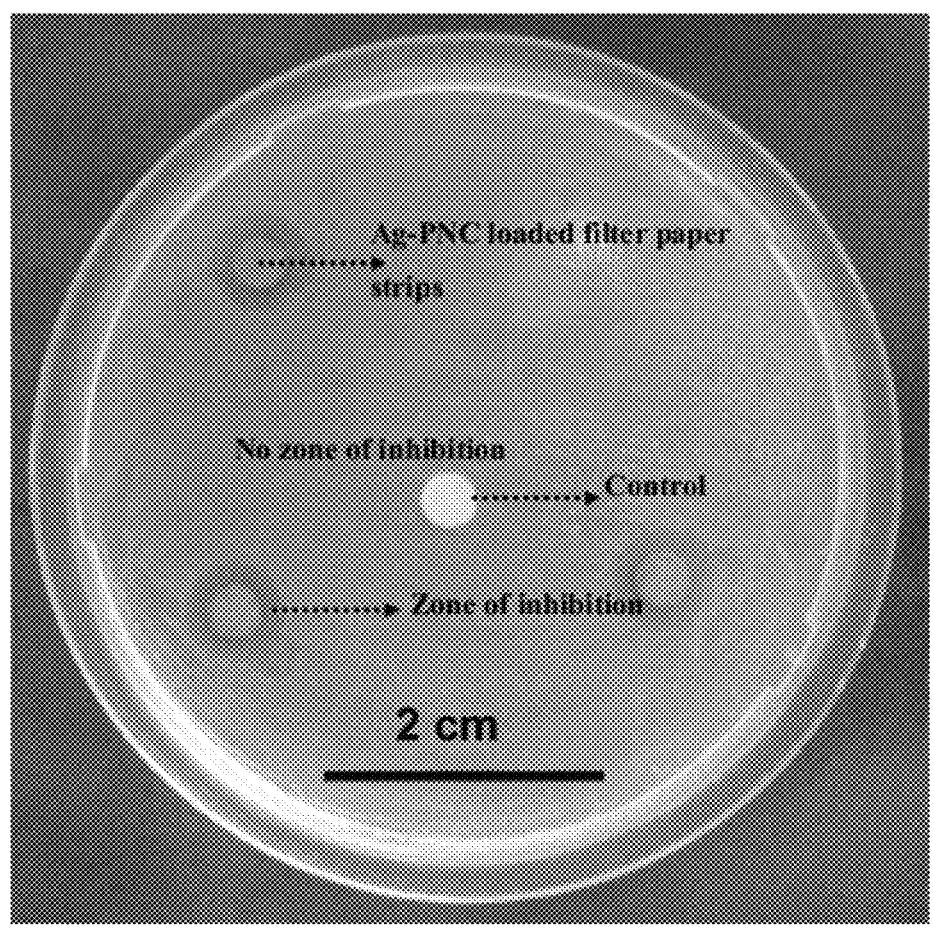
FIG. 2 shows the antibacterial activity of the Ag-PNC loaded on three filter paper discs against $E.\ coli$ bacteria.

The Ag-PNCs are antimicrobial and the antimicrobial property is static. That is, the Ag-PNCs of the embodiments herein show static antimicrobial activity (antimicrobial action persists for months). FIG. 2 shows the antibacterial activity of an example composition having Ag-PNC loaded on three filter paper discs against E. coli bacteria. The extent of antibacterial activity can be determined from measuring the zone of inhibition. In an example experiment, the width of the zone of inhibition measured persisted for several months with 10% or less change in the width of the zone of inhibition measured. This example experiment showed that the Ag-PNCs exhibited static antibacterial activity. On the other hand, an example experiment using the control (the disc without the Ag-PNC) showed an absence of the zone of inhibition. In the control example, the width of the zone of inhibition measured initially was zero and after two weeks the width measured was again zero.

In an embodiment, Ag nanoparticles (in aqueous phase) are treated with alkoxybenzyl halides (RO-BzX) in presence of an alcohol, polycondensation of the monomers occurs on the surfaces of the Ag nanoparticles resulting in Ag-PNCs, which are freely soluble in organic solvents (benzene ($C_6H_6$), toluene ($C_6H_5$-$CH_3$), dimethylformamide (DMF), dimethylsulfoxide (DMSO), tetrahydrofuran (THF), chlorobenzene, dichloromethane ($CH_2Cl_2$) and chloroform ($CHCl_3$)).

The alkoxybenzyl halides include alkoxybenzyl halides (2-methoxybenzyl chloride, 3-methoxybenzyl chloride, 4-methoxybenzyl chloride, and their bromides and iodides and ethoxy derivatives), alkylbenzyl halides (4-methylbenzyl chloride, 2-methylbenzyl chloride, 2,4-dimethylbenzyl chloride, 2,4,6-trimethylbenzyl chloride, and other alkyl derivatives), hydroxybenzyl halides (2, 3 and 4-hydroxybenzyl halides), and halohydroxybenzyl halides.

In an example embodiment the amount of Ag nanoparticles or the polymer in the Ag-PNCs can be varied to the desired level by changing the amount of the precursors during synthesis. The weight ratio of Ag nanoparticles to the polymer in the Ag-PNCs could vary from 0.001 to 0.000001, preferably from 0.01 to 0.00001, and more preferably from 0.1 to 0.01.

The Ag-PNCs can be applied in fields ranging from water treatment, purification, waste-water industry, military industry, civilian protection, soft drinks industry, detergents and hygiene industry, medical products, electrical, and electronics industry.

EXAMPLES

In an example embodiment, the polymerization reaction including the reaction chemistry can be as follows:

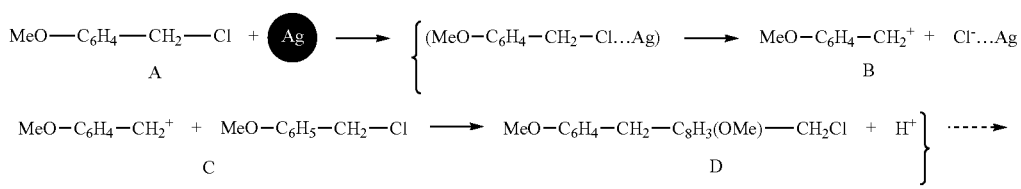

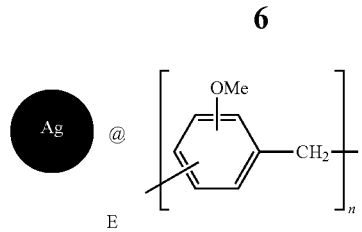

E

The alkoxybenzyl halides adsorb on Ag nanoparticles resulting in the formation of carbocations and halide anions. The carbocations react with fresh methoxybenzyl halides to form dimers as shown in the schematic. The dimers and trimers formed during the course of the reaction react further and form polycondensation products on nanosurfaces resulting in Ag-PNCs. The method of synthesis does not produce any harmful side products and most of the processing uses only water. Note that external catalysts required for polymerization of the monomers in reported/patented cases are avoided in the synthesis disclosed herein as the nanoparticle itself can also be functioning as a catalyst to the polycondensation reaction. During the polymerization reaction shown above, alkoxybenzyl halides undergo polycondensation on the nanosurfaces leading to Ag-PNCs. The polymer formed is poly (methoxybenzyl).

The presence of Ag nanoparticles and the polymer in the composites was confirmed by spectroscopy and microscopy. The spectroscopy and microscopy provided the evidence for the polycondensation on nanosurfaces resulting in Ag-PNCs.

Figure 3:
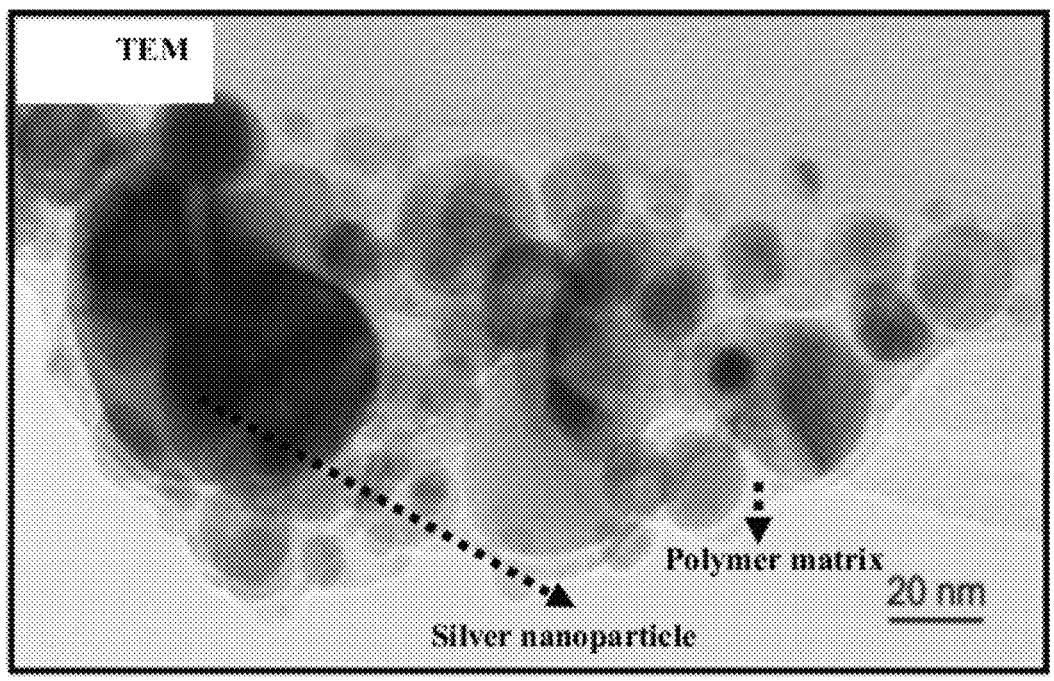
FIG. 3 shows a transmission electron micrograph of an Ag-PNC composite.

FIG. 3 shows a transmission electron micrograph (TEM) of an example Ag-PNC composite. FIG. 3 shows layers of the polymer and the embedded nanoparticles.

Figure 4:
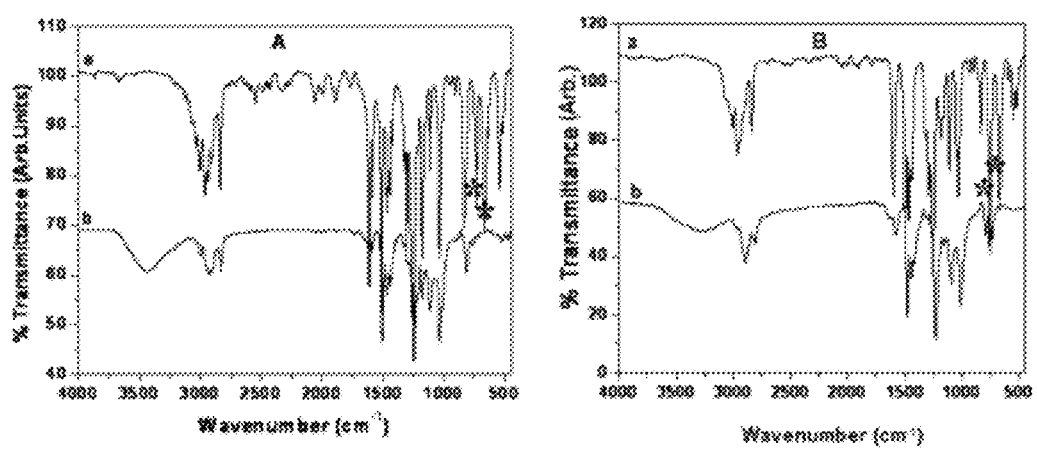
FIG. 4A and FIG. 4B show the IR spectra of the monomers (traces a) and the Ag-PNCs (traces b).

FIG. 4A and FIG. 4B show the IR spectra of the monomers (traces a) and the Ag-PNCs (traces b). The monomer in FIG. 4A is 4-methoxybenzyl chloride and that in FIG. 4B is 2-methoxybenzyl chloride. The C—Cl feature of the methoxybenzyl chloride (starred peaks) disappeared due to the polycondenzation reaction. The IR features of the polymers showed slight shifts from those of the methoxybenzyl chlorides due to their proximity to the nanoparticles' surfaces.

Figure 5:
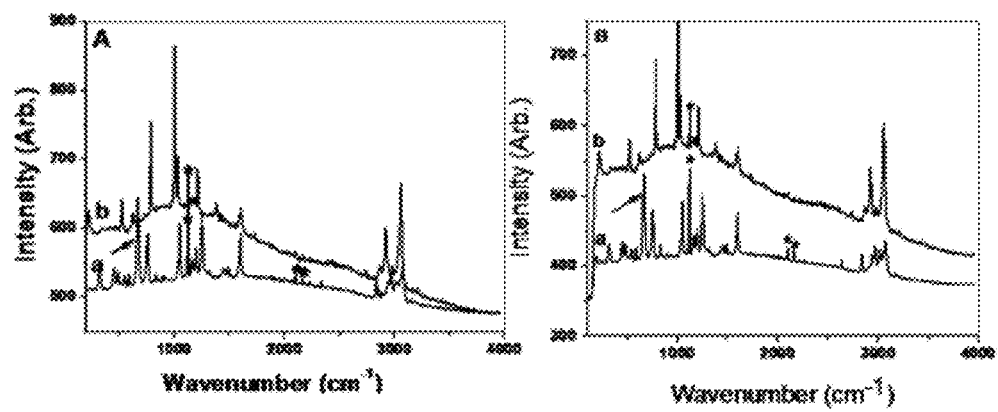
FIG. 5A and FIG. 5B show the Raman spectra of the monomers (traces a) and the Ag-PNCs (traces b).

FIG. 5A and FIG. 5B show the Raman spectra of the monomers (traces a) and the Ag-PNCs (traces b). The monomer in FIG. 5A is 4-methoxybenzyl chloride and that in FIG. 5B is 2-methoxybenzyl chloride. The C—Cl feature of the monomer (indicated with an arrow) disappeared in the polymer due to polycondensation. The starred peaks are from glass substrates on which the samples were deposited for Raman measurements. The Raman features of the polymers are enhanced in intensity due to the Surface Enhanced Raman Effect (SERS).

Figure 6:
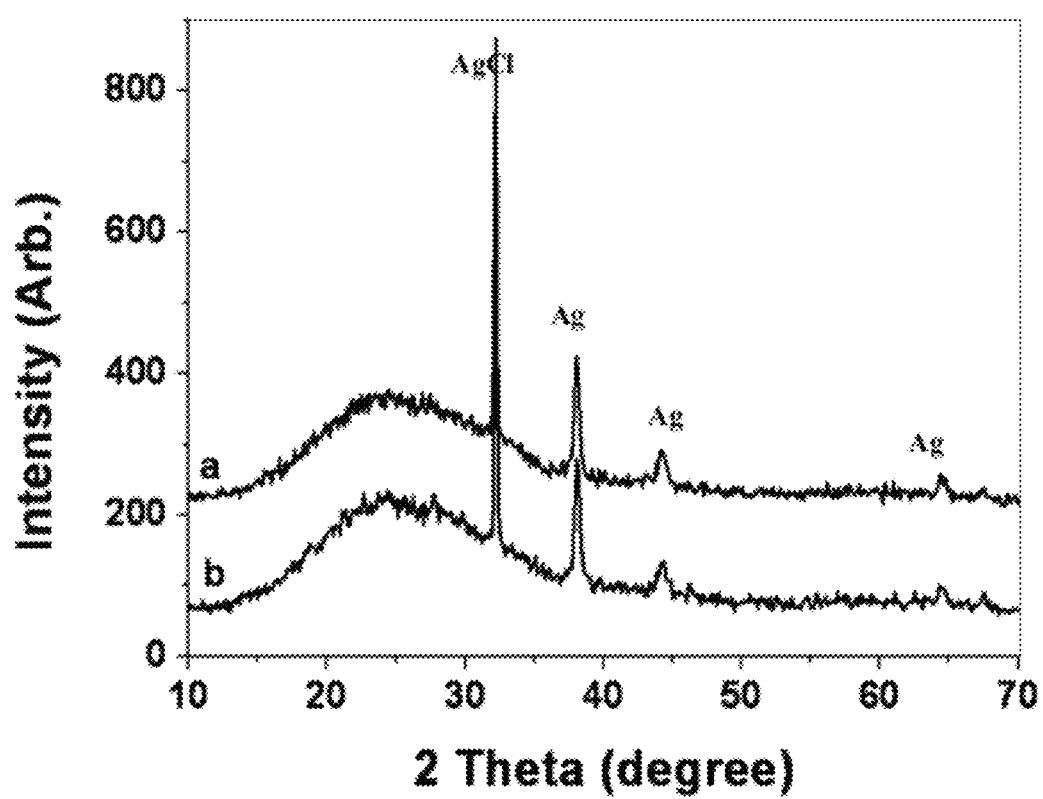
FIG. 6 shows the X-ray diffractograms of the Ag-PNCs, wherein the polymers were made from 4-methoxybenzyl chloride monomer (trace a) and 2-methoxybenzyl chloride monomer (trace b).

FIG. 6 shows the X-ray diffractograms (XRD) of the Ag-PNCs, wherein the polymers were made from 4-methoxybenzyl chloride monomer (trace a) and 2-methoxybenzyl chloride monomer (trace b). Major peaks are assigned in the spectra. XRD of the Ag-PNCs indicates the presence of Ag and AgCl. AgCl is also formed along with Ag-PNCs as a result of the polycondensation on Ag nano surfaces.

FIG. 7A shows the NMR spectrum of 2-methoxybenzyl chloride and FIG. 7B shows the NMR spectrum of the Ag-PNC formed from the 2-methoxybenzyl chloride monomer. The peaks corresponding to —OMe, —CH$_2$ and -Ph are broadened in the Ag-PNCs, typical of polymerization reactions.

In the detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

The invention claimed is:

1. A composition comprising a noble-metal containing nanoparticle and a polymer located on a surface of the nanoparticle, wherein the polymer is a poly(alkoxybenzyl) represented as:

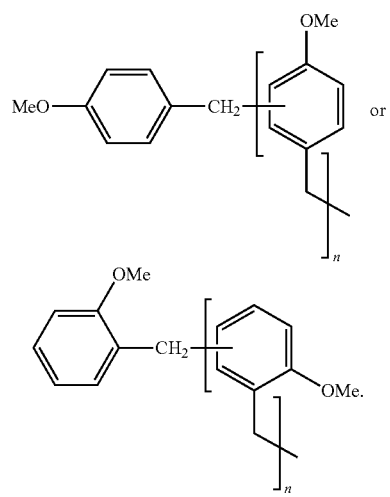

2. The composition of claim 1, wherein the composition exhibits an antimicrobial activity.

3. The composition of claim 1, wherein the composition dissolves in an organic solvent.

4. The composition of claim 1, wherein the polymer is located directly on the surface of the nanoparticle, wherein the nanoparticle comprises silver.

5. A method of preparing a composition of a noble-metal containing nanoparticle and a polymer, the method comprising: condensing a halogenated monomer in the presence of the noble-metal containing nanoparticle and forming the polymer from the halogenated monomer on a surface of the noble-metal containing nanoparticle, wherein the method is carried out in a single vessel, and the polymer is a poly(alkoxybenzyl) represented as:

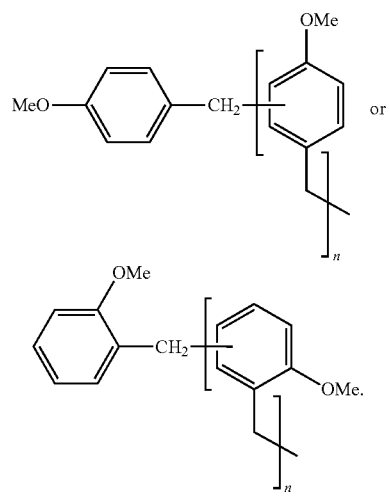

6. The method of claim 5, wherein the method is carried out at about room temperature.

7. The method of claim 5, wherein the polycondensation comprises a chemical condensation reaction leading to a formation of the polymer by polymerizing the monomer and releasing water or a molecule.

8. The method of claim 5, wherein the nanoparticle comprises silver and the monomer comprises an alkoxybenzyl halide.

9. The method of claim 5, wherein the forming the polymer is carried out without a presence of an external catalyst during the polycondensation of the monomer.

10. The method of claim 5, wherein the polymer is located directly on the surface of the nanoparticle, wherein the nanoparticle comprises silver.

11. A method of antimicrobial treatment of a material in need thereof, the method comprising treating the material with a composition comprising a noble-metal containing nanoparticle and a polymer located on a surface of the nanoparticle, wherein the polymer is a poly(alkoxybenzyl) represented as:

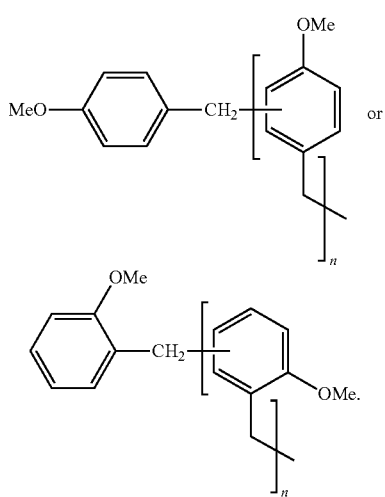

12. The method of claim 11, wherein the treating is an antimicrobial treatment.

13. The method of claim 11, wherein the material is selected from water, waste water, a military equipment, a civilian protection equipment, a soft drink, a detergent, a medical product, an electrical component, an electronics component, and combinations thereof.

14. The method of claim 11, wherein the treating comprises applying a film or a coating on the material, the film or the coating comprising the composition.

15. The method of claim 11, wherein the treating comprises reducing an amount of bacteria and/or fungi in or on the material.

16. The method of claim 12, wherein the antimicrobial treatment produces antimicrobial activity that persists for at least one month.

17. The method of claim 11, wherein the nanoparticle comprises silver.

* * * * *

UNITED STATES PATENT AND TRADEMARK OFFICE
CERTIFICATE OF CORRECTION

PATENT NO.         : 8,268,359 B2                                   Page 1 of 1
APPLICATION NO.    : 12/639403
DATED              : September 18, 2012
INVENTOR(S)        : Pradeep et al.

It is certified that error appears in the above-identified patent and that said Letters Patent is hereby corrected as shown below:

On the Title Page, in Item (56), under "OTHER PUBLICATIONS", in Column 2, Line 6, delete "Polyacryamide-Stabilized" and insert -- Polyacrylamide-Stabilized --, therefor.

In the Specification

In Column 1, Line 21, delete "processibility" and insert -- processability --, therefor.

In Column 3, Line 25, delete "polycondenzation." and insert -- polycondensation. --, therefor.

In Column 3 & 4, delete

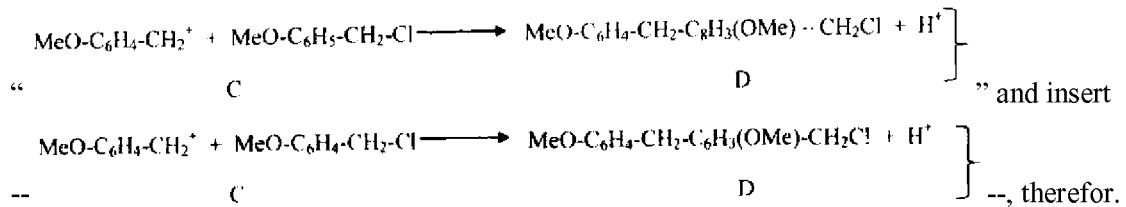

" and insert -- --, therefor.

In Column 5, Line 39, delete "polycondenzation" and insert -- polycondensation --, therefor.

In Column 5, Line 51, delete "Effect" and insert -- Spectroscopy --, therefor.

Signed and Sealed this
Seventeenth Day of September, 2013

Teresa Stanek Rea
*Deputy Director of the United States Patent and Trademark Office*